United States Patent [19]

Carpel

[11] Patent Number: 4,465,066

[45] Date of Patent: Aug. 14, 1984

[54] SURGICAL DRAPE SUPPORT

[76] Inventor: Emmett F. Carpel, 2683 E. Lake of the Isles Blvd., Minneapolis, Minn. 55408

[21] Appl. No.: 347,190

[22] Filed: Feb. 9, 1982

[51] Int. Cl.$^3$ .............................................. A61B 19/08
[52] U.S. Cl. ............................ 128/132 D; 128/76 C; 128/206.16; 604/304
[58] Field of Search ............ 128/132 R, 132 D, 76 C, 128/163–164, 201.18, 206.16, 206.18, 206.21, 206.25, 207.13; 604/303–304, 307–308; 351/124–125

[56] References Cited

U.S. PATENT DOCUMENTS

| | | | |
|---|---|---|---|
| 1,100,991 | 6/1914 | Bostow | 128/76 C |
| 3,297,034 | 1/1967 | Peavy | 604/307 X |
| 3,426,751 | 2/1969 | Radewan | 128/76 C |
| 3,695,265 | 10/1972 | Brevik | 128/132 X |
| 4,122,848 | 10/1978 | Carpel | 128/132 D |

Primary Examiner—Lee S. Cohen
Assistant Examiner—Angela D. Sykes
Attorney, Agent, or Firm—Hugh D. Jaeger

[57] ABSTRACT

Surgical drape support for use in eye surgery or other surgery, providing for free and clear support of a surgical drape with respect to the patient's nostrils and mouth. The surgical drape support is a three-membered T device for securing to each side of the cheek and to the bridge of the nose. Adhesive pads positioned on each of the members provide for securing of the support to the cheeks and nose. The leg of the T which secures to the nose is indented providing for three-point engagement about the nose, enhancing stability of structural support of the surgical drape support.

9 Claims, 5 Drawing Figures

SURGICAL DRAPE SUPPORT

BACKGROUND OF THE INVENTION

1. Field of the Invention

Present invention pertains to a surgical instrument and, more particularly, pertains to a surgical drape support for use during eye surgery or other facial surgery.

2. Description of the Prior Art

During surgery, especially eye surgery, it is always an immense problem in the operating theater during surgery to keep a surgical drape free and clear of the individual's nostrils and mouth. It is common that the prior art devices have failed to reliably do so and as most commonly happens during the surgery, the individual tends to inhale air through the mouth or nostrils, thereby creating a low-pressure area which sucks in the drape and further plugging the air passages. Subsequently the patient grasps for large amounts of air and further creates lower pressures, thereby further sucking in the surgical drape support to the nostrils or mouth which is disruptive during the surgery, disruptive to the aneasthesiologist, and, most particularly, very disruptive to the surgeon who has to stop the surgical procedure to clear the passages so as not to suffocate the patient. Of particular importance during a surgical procedure, the patient may thrash about trying to consciously or unconsciously free the surgical drape leading to injury through ill-placed incisions, etc., based on the patient's movement.

The prior art devices have usually been cumbersome and bulky support structures which hamper the freedom of movement of the surgeon during the surgery. The prior art devices have been high physical profile support structures, thereby limiting the freedom of movement of the surgeon's hands during surgery in the operating theater.

Other prior art devices have only been a single bar member having two positions of support about the cheek which provides for vertical movement of the surgical drape and does not clearly provide for free passage and flow of air about an individual's nostrils.

Other prior art devices have been surgical supports which are not disposable and require sterilization.

A representative prior art surgical drape support is illustrated in U.S. Pat. No. 4,122,848 entitled "Surgical Drape Support," issued to Emmett F. Carpel, M.D. This prior art is representative of the most advanced and effective prior art surgical drape support available and has been published in the *Academy Journal of Ophthalmology*.

The present invention overcomes the disadvantages of the prior art devices by providing a surgical drape support which is disposable and provides for stability through three anchoring points to the inddividual while maintaining free and unobstructed passage of an individual's nostrils and mouth.

SUMMARY OF THE INVENTION

The general purpose of the present invention is to provide a surgical drape support which includes three points of anchor to an individual's nose and sides of the cheeks through adhesive pads, and provides for support of a surgical drape over, free and clear of an individual's nostrils and mouth.

According to one embodiment of the present invention, there is provided a surgical drape support including a three-member T-shaped support, adhesive pads at each end of the longitudinal member, side triangular projections affixed on each side of the end of a leg member, and small adhesive tabs affixed to each triangular member and the leg member, small indentations provided along each side of the joint between each of the triangular side projections and the end leg member whereby the triangular projections secure to each side of the nose, the leg member secures to the bridge of the nose, and the elongated member secures to each side of the cheek, thereby providing for three-barred secured support over an individual's nostrils and mouth and free and clear air flow.

A significant aspect and feature of the present invention is a three-bar surgical drape support which provides for a low-profile drape support and also provides for free and clear unrestricted air passage about an individual's nostrils and mouth.

Another significant aspect and feature of the present invention is a surgical drape support which provides for stability and support of a surgical drape particularly during eye surgery.

A further significant aspect and feature of the present invention is a surgical drape support which is sterilizable and shippable in a flat package, and is conforming to a three-dimensional structure upon securing to an individual during surgery in the operating theater. The surgical drape support lends itself to disposability after operation including low cost of use to the patient.

Having thus described the invention, it is a principal object hereof to provide a surgical drape support.

An object of the present invention is to provide a surgical drape support which is adjustable to any size individual and conforming to an individual's head shape.

Another object of the present invention is to provide a surgical drape support which provides for stability and support of the surgical drape while also providing a low-profile structural support of the surgical drape thereby providing the necessary freedom of movement of the surgeon during surgical procedures in the operating theater.

BRIEF DESCRIPTION OF THE DRAWINGS

Other objects and many of the attendant advantages of this invention will be readily appreciated as the same becomes better understood by reference to the following detailed description when considered in connection with the accompanying drawings, in which like reference numerals designate like parts through the figures thereof and wherein.

DESCRIPTION OF THE PREFERRED EMBODIMENTS

Figure 1:
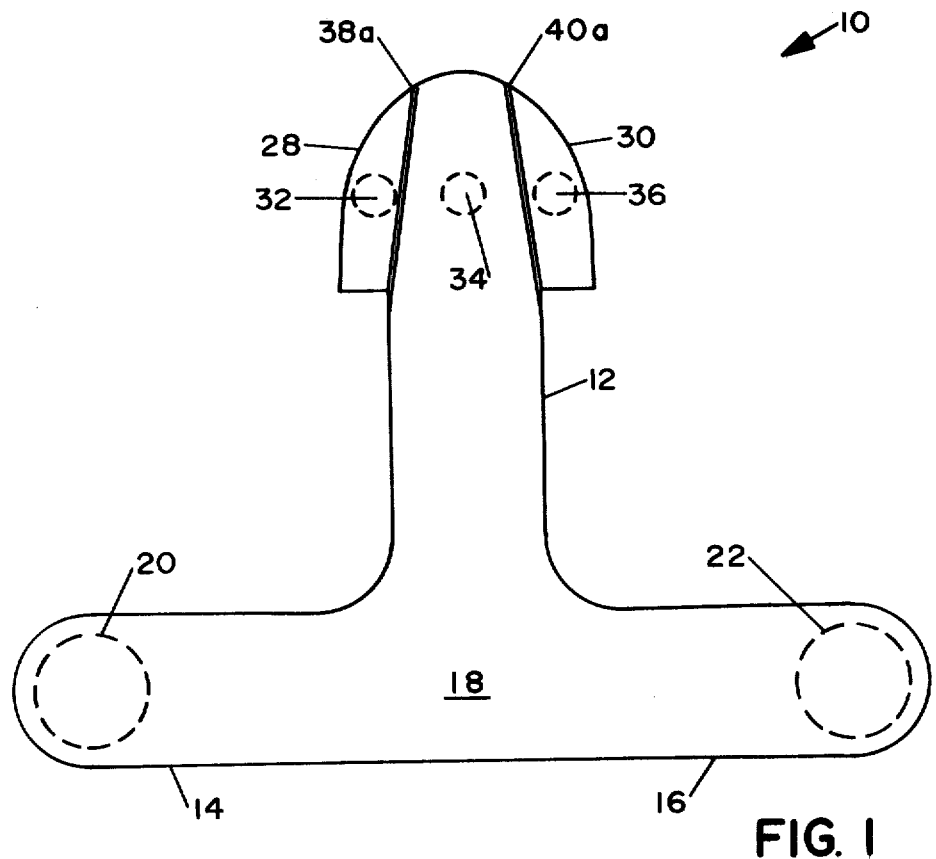
FIG. 1 illustrates a top plan view of a surgical drape support, the present invention.
Figure 2:
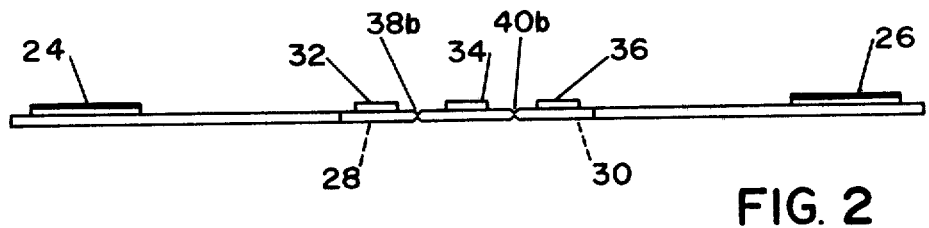
FIG. 2 illustrates a side view of a surgical drape support.

FIG. 1, which illustrates a plan view of a surgical drape support 10, the present invention, shows a three-barred T-member device including members 12, 14 and 16. The members 14 and 16 comprise an elongated longitudinal member 18. Round circular dots 20 and 22 of double-sided adhesive secure to opposite ends of the elongated member 18 and can include suitable protective shields 24 and 26 as illustrated in FIG. 2 for protecting the three adhesive backing. The leg member 12 includes side triangular projections 28 and 30 which can be any other geometrical configuration than triangular as disclosed, by way of example and for purposes of illustration only and not to be construed as limiting of the present invention. Like dots of adhesive 32, 34 and 36, indentations 38a and 40a and 38b and 40b are provided on either side of the intersection of the projections 28 and 30 with the leg member 12. Depending upon the particular materials, indentations may only need be provided on the bottom or top of the drape support.

The surgical drape support 10 can be constructed of either heavy stock paper material, cardboard material, or like polyethylene material. The particular choice of material lends itself to either heavy pressboard or plastic material. The adhesive can be any suitable double-sided adhesive dots or other geometrical configurations providing the required degree of stickiness between an individual's skin and the chosen material for the surgical drape support 10.

FIG. 2 illustrates a side view showing numerals which correspond to those elements previously described.

PREFERRED MODE OF OPERATION

Figure 3:
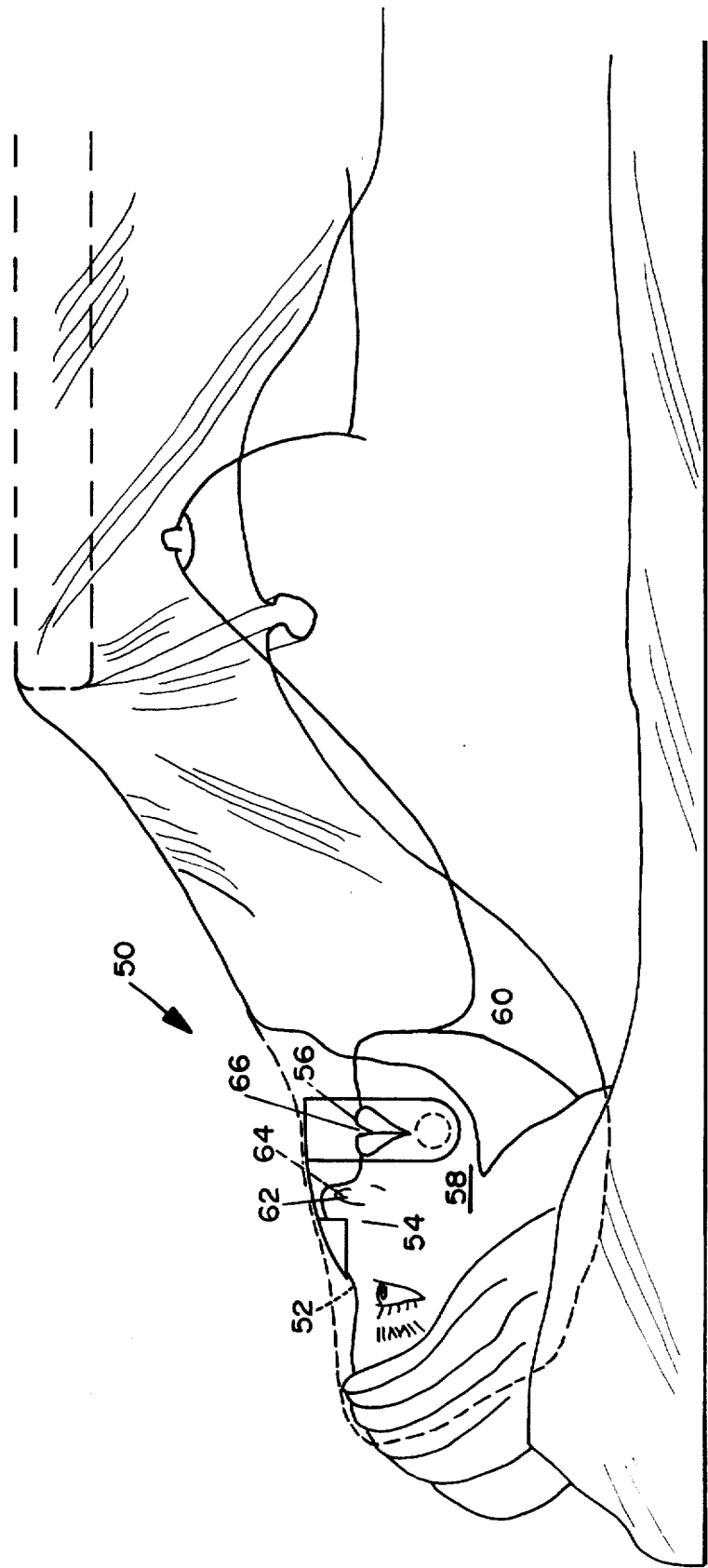
FIG. 3 illustrates the surgical drape support in position and secured to an individual's head during surgery in the operating theater.

FIG. 3 illustrates a surgical drape support in position over an individual's frontal facial portion 50 positioned about the bridge 52 of an individual's nose 54, about the mouth 56, and secured to the cheeks 58, and 60. The adhesive pads 32 and 34 are clearly shown bridging the surgical drape support, leg member 12 and triangular portions 28 and 30 providing for three-point placement and securing about the nose. The adhesive pads 20 are shown securing one bar 14 to the cheek 58. It is seen that the nostrils 62 and 64 of the nose 54 and the air passage 66 of the mouth 56 are free and clear, providing for unrestricted air flow. The three-bar members 12, 14 and 16 provide for effective triangular support about the nostrils 62 and 64 and the mouth 56. The three-bar support further provides for support in non-movement or collapsing of the surgical drape about or between the nose 54 and the mouth 56.

The drape support lends itself to construction from either pressboard or bendable cardboard which will assume and memorize a predetermined geometrical configuration or from light plastic or suitable other material which exhibits flexibility in assuming a three dimensionable predetermined geometrical shape. Depending upon whether the patient is a child or adult, or on the head size of the individual, it may be necessary to provide two or three sizes of surgical drape supports. The surgical drape supports are intended to be disposal, can be packaged in Tyvek envelopes, and sterilized by ETO or any other acceptable procedure.

DESCRIPTION OF A FIRST ALTERNATIVE EMBODIMENT

Figure 4:
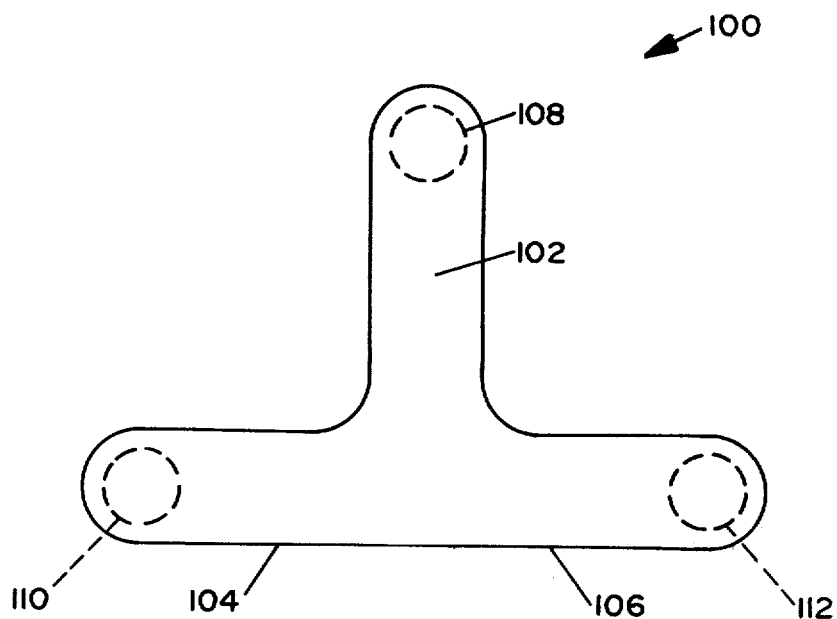
FIG. 4 illustrates a first alternative embodiment of the present invention; and, FIG. 5 illustrates a second alternative embodiment of the present invention, the surgical drape support for four point placement with a four bar member.

FIG. 4 illustrates a first alternative embodiment 100 of a plan view of the present invention showing a three bar member 102, 104, and 106 support member with adhesive spots 108, 110, and 112 on one side of the three bar member 100. The figure shows that the alternative member 100 is similar to that of FIGS. 1-3 with the exception of the elements 28, 30, 32, and 36, but identical in operation.

FIG. 4 in operation is identical to that of FIGS. 1-3 in that the surgical drape support 100 is affixed to three points of the head for support; that is, the bridge of the nose, and opposing sides of the cheeks.

FIGS. 1-3 and FIG. 4 provide for room for surgical tubes or masks of the surgeon or more importantly, the anesthesiologist. The three bar support provides volume of space for flow of air through the nose and mouth even with the drape supported above the nose and mouth. The fold lines and triangular member member from the nose portion of the support of FIGS. 103 can also be added to the nose bar 102 while the cheek bars 104 and 106 would remain identical in structure.

DESCRIPTION OF A SECOND ALTERNATIVE EMBODIMENT

Figure 5:
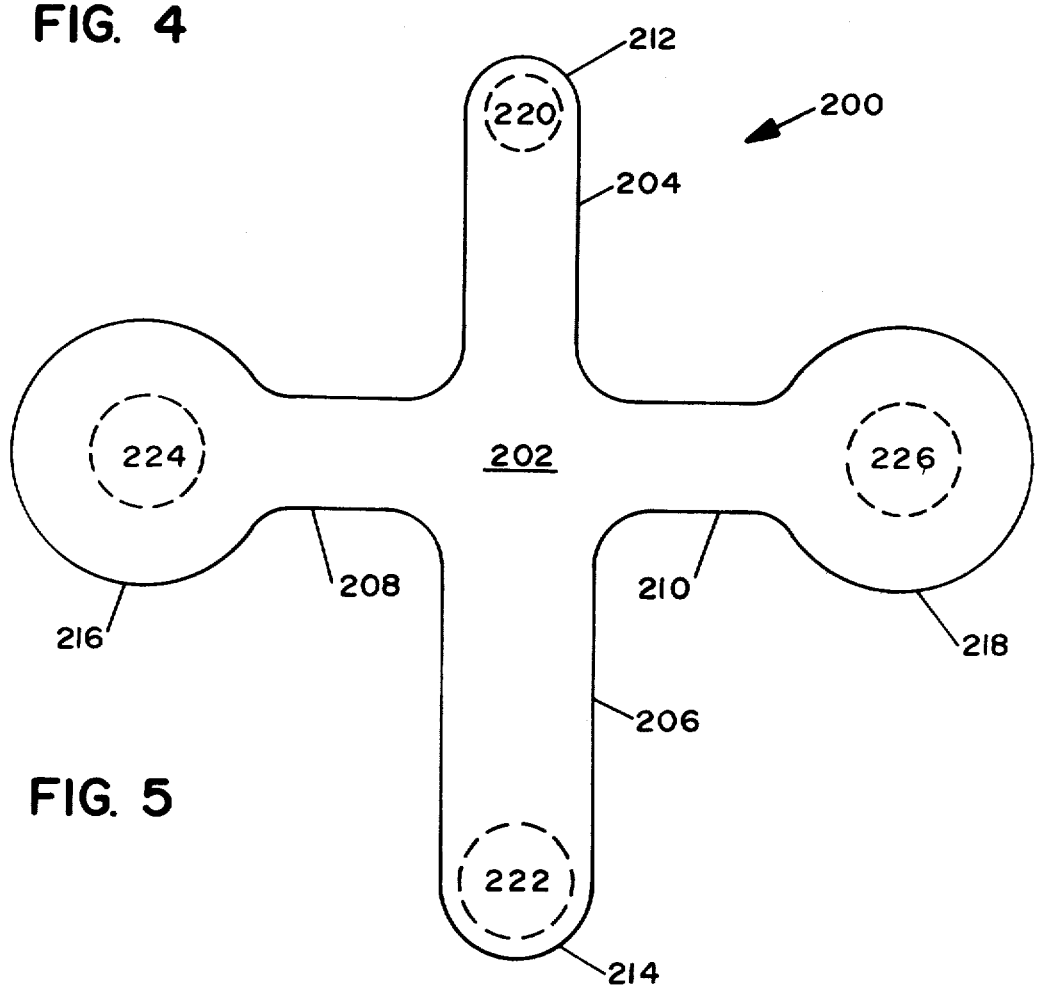

FIG. 5 illustrates a second alternative embodiment 200 of a plan view of the present invention showing a junction 202 for a four bar member 204, 206, 208, and 210. Bars 204 and 206 have rounded ends 212 and 214 and bars 208 and 210 have enlarged rounded ends 216 and 218 for fastening to the cheeks. Rounded circular pads 220, 222, 224, and 226 are provided at the ends of each of the ends of each bar. Bar 206 can be slightly longer than the other bars in that this bar loops over the chin and secures under the chin with the adhesive pad. The enlarged rounded ends can also be used with the embodiments of FIGS. 1-3 or 4. The fold lines and triangular member from the nose portion can also be added to bar 204 as taught in FIGS. 1-3.

FIG. 5 in operation is identical to that of FIGS. 1-3 in that the surgical drape support 200 is affixed to four points of the head; that is, the bridge of the nose, each opposing side of the cheek over the mouth, and under the chin providing for four point anchoring about, over and around the mouth. The four bar point provides to total securing of volume over the nose and mouth providing for a free and secure air passage even with the drape support above the nose or mouth.

Various modifications can be made to the present invention without departing from the apparent scope thereof. The surgical drape support can be made from any suitable material which assumes and memorizes a three dimensional shape over and about the patient's mouth and nose air passages. The size, shape, and diameter of adhesive pads is determined by the type of material and the size of the surgical drape support dependent upon the individual's head size. The crease or fold lines can be suitably positioned in any of the bars and are not solely limited to only between the triangular members and the bar as illustrated in FIGS. 1-3. Other crease and fold lines can be provided in the other bars for bending the members in a rectangular or any other predetermined geometrical shape. The triangular portions extending from the end of the leg member of the T-bar member can assume any configured geometrical configuration with appropiate crease fold lines providing for packinging in a substantially flat package and a three dimensional configured surgical drape support in use in the operating theater.

Having thus described the invention, what is claimed is:

1. Surgical drape support for supporting a surgical drape over an individual's nose and mouth comprising:

a. means providing for configured three-point support from the bridge of an individual's nose and over and above said nose and mouth of an individual's face including a three-bar T-member support having one leg bar member secured to a substantially mid portion of an elongated bar member of said T; said leg bar member at least of a length for extending from said bridge to a point at least over said mouth of said individual;

b. means providing for at least-one point support of an end of said leg bar member for positioning at, over and about said bridge of said individual's nose; and, c. means for adhesively securing each end of said elongated bar member to opposing sides of an individual's cheeks and at least one point about said bridge of said individual's nose whereby said three-bar support provides for support of a surgical drape thereby providing for free, clear and unobstructed passage of air through said individual's nostrils and mouth and preventing said surgical drape from being sucked into the individual's mouth during surgery thereby preventing suffocation.

2. Support of claim 1 including three-point means at said end of said leg bar member and two triangular configured side projections affixed thereto forming a junction, and adhesive means affixed to each of said triangular projections.

3. Support of claim 2 wherein indentations are provided between the junction of said side triangular projections and said end of said leg bar member.

4. Support of claim 1 wherein said adhesive securing means comprises dots of adhesive affixed to each of said ends of said elongated bar member, and each of said side projections.

5. Support of claim 1 wherein each of said adhesive means includes a protective member for removal prior to affixation to an individual.

6. Support of claim 1 wherein said means for providing three-point support is pressboard.

7. Support of claim 1 wherein said means for providing three point support is made of plastic.

8. Support of claim 1 including an enlarged bar rounded end on each end of said elongated bar member.

9. Support of claim 1 including an additional bar with adhesive means, said additional bar being at a junction of said T member and extending downwardly whereby said additional bar is adapted to be secured to an individual's chin thereby providing a form bar support.

* * * * *